United States Patent [19]
Hart et al.

[11] Patent Number: 5,402,665
[45] Date of Patent: Apr. 4, 1995

[54] MONITORING GASEOUS OXYGEN CONCENTRATION

[76] Inventors: Russell F. Hart, 9104 130th St., Blue Grass, Iowa 52726; Tuan Q. Cao, 3238 W. Denison Ave., Davenport, Iowa 52804

[21] Appl. No.: 66,275

[22] Filed: May 11, 1993

[51] Int. Cl.$^6$ ............... G08B 17/10; G01D 18/00; G01N 27/00
[52] U.S. Cl. ................... 73/16; 73/23.2; 340/632
[58] Field of Search ........... 73/1G, 23.31, 31.05, 73/31.06, 23.2; 340/632, 633, 634

[56] References Cited

U.S. PATENT DOCUMENTS

| | | | |
|---|---|---|---|
| 4,109,509 | 8/1978 | Cramer et al. | 73/23.3 |
| 4,189,725 | 2/1980 | Rowland | 73/31.05 |
| 4,235,096 | 11/1980 | Yasuda et al. | 73/23.31 |
| 4,352,087 | 9/1982 | Wittmaier | 73/31.05 |
| 4,390,869 | 6/1983 | Christen et al. | 340/634 |
| 4,442,698 | 4/1984 | Alftine | 73/24.01 |
| 4,455,861 | 6/1984 | Alftine | 73/31.04 |
| 4,464,653 | 8/1984 | Winner | 73/23.2 |
| 4,481,804 | 11/1984 | Eberhard et al. | 73/1G |
| 4,499,914 | 2/1985 | Schebler | 137/81.1 |
| 4,779,446 | 10/1988 | Rowland | 73/1G |
| 4,854,153 | 8/1989 | Miyagawa et al. | 73/1G |
| 4,995,256 | 2/1991 | Norlien et al. | 73/31.05 |
| 5,071,453 | 12/1991 | Hradek et al. | 96/111 |
| 5,034,725 | 7/1991 | Sorenson | 73/23.2 |

OTHER PUBLICATIONS

"STD Bus Oxygen Analyzer", Litton ILSD, Commercial Products, Pub. No. 10408A (1993).

*Primary Examiner*—Hezron E. Williams
*Assistant Examiner*—Michael J. Brock

[57] ABSTRACT

Apparatus for monitoring gaseous oxygen concentration that includes an oxygen sensor for providing an electrical sensor signal that varies as a function of oxygen concentration at the sensor. Processor circuitry compares oxygen concentration indicated by the sensor signal to at least one threshold level, and indicates when such oxygen concentration at the sensor departs from such threshold concentration level. The apparatus is calibrated by exposing the sensor to a calibration gas having an oxygen concentration equal to the desired threshold concentration level, and storing in the processor circuitry electrical indicia indicative of operating characteristics of the sensor at such threshold oxygen concentration level. When the apparatus is thereafter employed for monitoring a gas of undetermined oxygen concentration, the operating characteristics of the sensor reflected by the sensor output signal are compared to the prestored indicia for determining when oxygen concentration at the sensor crosses the threshold concentration level.

5 Claims, 3 Drawing Sheets

MONITORING GASEOUS OXYGEN CONCENTRATION

The present invention is directed to monitoring of gaseous oxygen concentration, and more particularly to a method and apparatus for indicating when oxygen concentration in a monitored gas equals or departs from one or more threshold concentration levels.

BACKGROUND AND SUMMARY OF THE INVENTION

There are numerous applications in which it is desirable to indicate when gaseous oxygen concentration departs from—i.e., becomes either greater than or less than—one or more predetermined threshold concentration levels. For example, in the home health care environment, it is desirable to monitor the output of an oxygen concentrator to determine when the output oxygen level decreases below a minimum desired limit, such as eighty-five percent oxygen. In other industrial and commercial applications, it is desirable to maintain oxygen concentration between preset lower and upper limits. Current devices for monitoring oxygen concentration are expensive and subject to tampering at the application site. It is therefore a general object of the present invention to provide a method and apparatus for monitoring concentration of oxygen in a test gas and indicating when such concentration departs from one or more preselected threshold levels, which are inexpensive to manufacture and implement, which function reliably over an extended operating life, and/or which can be selectively reprogrammed at the factory or in the field by properly trained and equipped personnel while resisting tampering by unauthorized or untrained personnel.

Apparatus for monitoring gaseous oxygen concentration in accordance with a presently preferred embodiment of the invention comprises an oxygen sensor for providing an electrical sensor signal that varies as a function of oxygen concentration at the sensor. Processor circuitry compares oxygen concentration indicated by the sensor signal to at least one threshold level, and indicates when such oxygen concentration at the sensor departs from such threshold concentration level. The apparatus is calibrated by exposing the sensor to a calibration gas having an oxygen concentration equal to the desired threshold concentration level, and storing in the processor circuitry electrical indicia indicative of operating characteristics of the sensor at such threshold oxygen concentration level. When the apparatus is thereafter employed for monitoring a gas of undetermined oxygen concentration, the operating characteristics of the sensor reflected by the sensor output signal are compared to the prestored indicia for determining when oxygen concentration at the sensor crosses the threshold concentration level.

In the preferred embodiment of the invention, the processor circuitry is microprocessor-based and may be programmed to detect a plurality of oxygen concentration levels by sequentially exposing the sensor to calibration gas at the various oxygen concentration levels, and storing electrical indicia indicative of operation of the sensor at each such calibration level for later comparison to the sensor output during use. Such calibration operation preferably is performed at the time of manufacture, and the indicia of one or more calibration levels is stored in non-volatile memory for subsequent use in the field. The apparatus circuitry and the sensor are mounted on a circuitboard assembly, with the sensor and cardedge electrical contacts disposed along one edge of the board. The board may be plugged into calibration apparatus in which the contacts are connected to calibration control circuitry and the sensor is exposed to test gas at desired oxygen concentration through a manifold in the calibration apparatus. Recalibration in the field is either not possible, or requires special knowledge and equipment only possessed by a trained technician.

BRIEF DESCRIPTION OF THE DRAWINGS

The invention, together with additional objects, features and advantages thereof, will be best understood from the following description, the appended claims and the accompanying drawings in which:

DETAILED DESCRIPTION OF PREFERRED EMBODIMENTS

Figure 1:
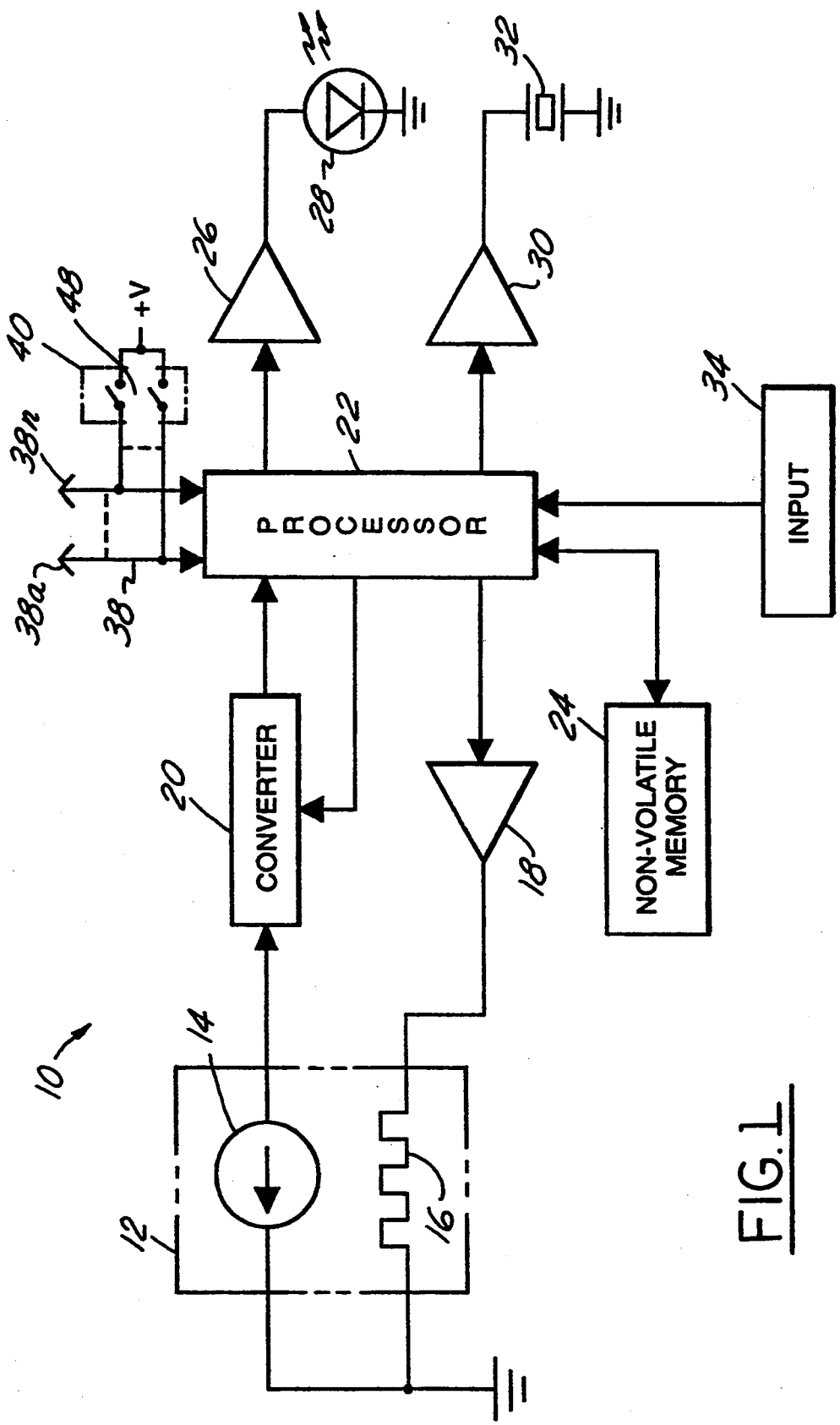
FIG. 1 is a functional block diagram of apparatus for monitoring oxygen concentration in accordance with one presently preferred embodiment of the invention.

FIG. 1 illustrates apparatus 10 for monitoring gaseous oxygen concentration in accordance with one presently preferred embodiment of the invention as comprising an oxygen concentration sensor 12 having a sensor element 14 of zirconium oxide or other suitable solid-state construction and a heater element 16 for raising the temperature of sensor element 14 to a suitable level above ambient. Heater 16 is energized by an amplifier 18 for raising the temperature of sensor 12 to a level of 400° C., for example, at which oxygen ions are mobile within the matrix of sensor element 14. Sensor element 14 thus provides an analog electrical current signal that varies as a function of oxygen concentration in the gas to which sensor 12 is exposed.

The sensor output signal is fed to a convertor 20, in which the analog input signal is converted to a format suitable for digital processing. In the preferred embodiments of the invention, the analog input signal is converted to a periodic signal having periodicity characteristics—i.e., time duration and/or frequency—that vary as a function of input current level. Such periodic signal indicative of oxygen concentration is fed as an input to a processor 22. Processor 22 is connected to a non-volatile memory 24 for selectively storing and retrieving calibration and measurement data. Processor 22 provides one output to a driver 26 for energizing an LED 28, and another output to a driver 30 for activating an audible alarm or buzzer 32. Processor 22 may also receive an external control input 34. Processor 22 also enables operation of convertor when sensor output sampling is required, as will be described.

Figure 4:
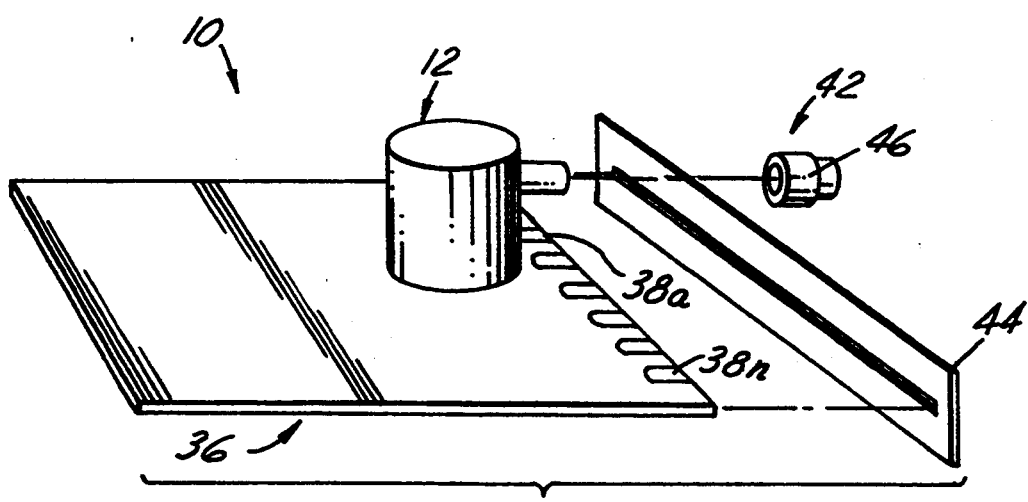
FIG. 4 is a perspective diagram that illustrates calibration of the apparatus of FIG. 1.

Apparatus 10 illustrated in FIG. 1 is most preferably provided in the form of a printed circuitboard assembly 36, as shown in FIG. 4, having sensor 12 mounted thereon. Processor 22 (FIG. 1) has an I/O bus 38 with lines connected to a series of card-edge contacts 38a–38n that extend in an array along one edge of assembly 36 adjacent to sensor 12. Bus 38 is also connected within assembly 36 to an on-board DIP-switch socket 40 (FIG. 1). Processor 22 and non-volatile memory 24 preferably are provided in the form of a single integral microprocessor having on-board non-volatile memory for storing operating software as well as sensor calibration indicia as will be described. Amplifier 18, drivers 26,30 and convertor 20 may be of any suitable construction. All components of FIG. 1 are on assembly 36, with the exception of input 35 in the preferred embodiment, which is the calibration unit to be described.

To calibrate apparatus 10 in accordance with one feature of the present invention, assembly 36 (FIG. 4) is plugged into a calibration fixture 42 that includes both a card-edge connector 44 for mating with contacts 38a–38n, and a connector 46 for supplying a calibration gas at predetermined oxygen concentration to sensor 12. With assembly 36 so inserted in calibration apparatus 42 and sensor 12 exposed to the calibration gas, processor 22 is activated by operator input 34 (which may be within calibration apparatus 42) for monitoring the output signal from sensor element 14 and storing in memory 24 electronic indicia indicative of operating characteristics of the sensor at the specific oxygen concentration of the calibration gas. This calibration procedure may be repeated by sequentially inserting assembly 36 in other calibration fixtures that expose sensor 12 to other calibration concentration levels, and sequentially storing in memory 24 indicia indicative of sensor operation at each such oxygen concentration level. Thus, the operating circuitry is calibrated for the characteristics of a particular sensor 12. Where multiple threshold levels are to be detected, multiple LED's 28 may be provided, or a single LED may be controlled based upon the relationship of the test gas to the multiple thresholds (as for instance inside or outside of a range). Thereafter, processor 22 monitors sensor 12 and energizes LED 28 and/or buzzer 32 when oxygen concentration either exceeds or decreases below one of the calibration levels.

Figure 2:
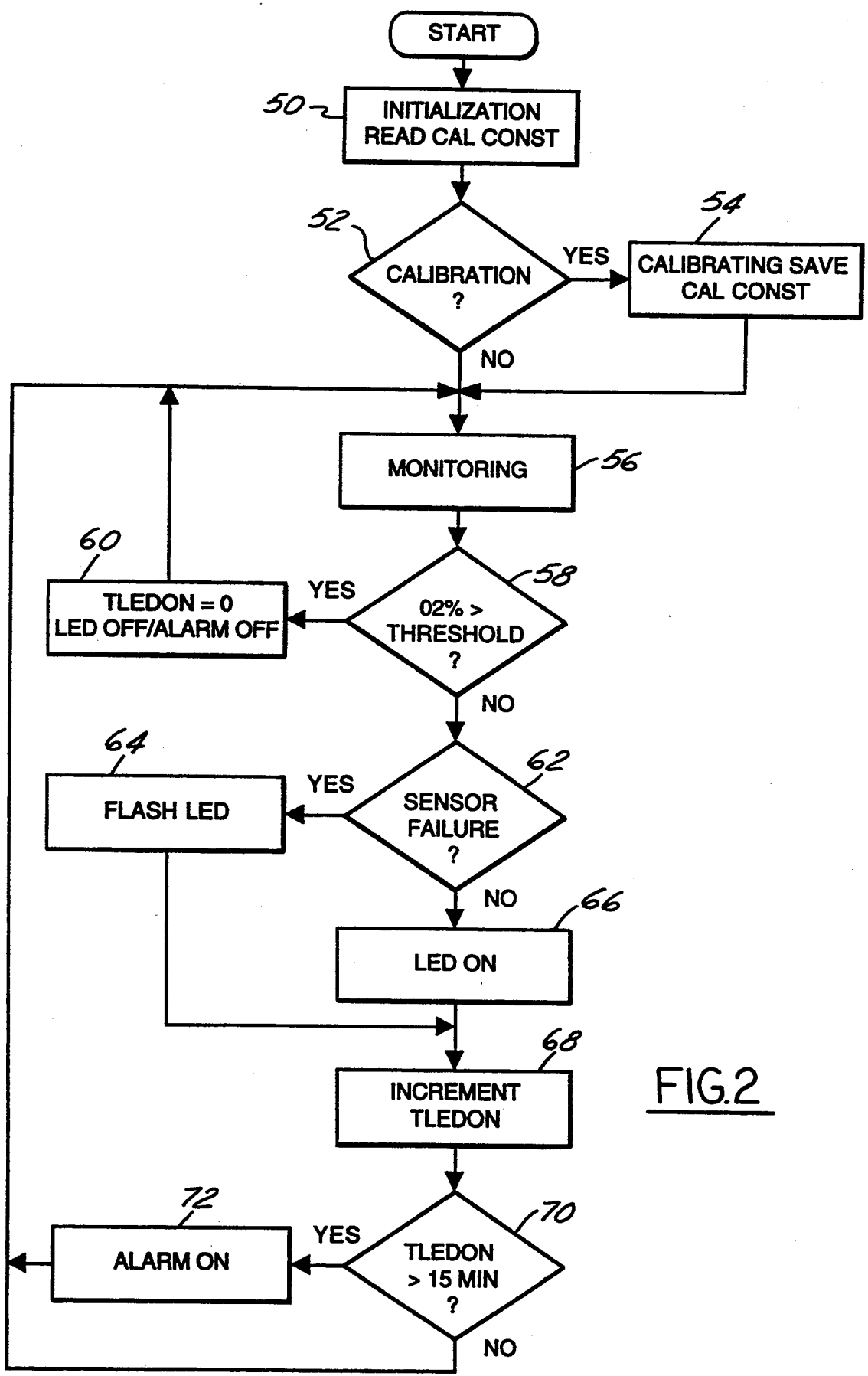
FIG. 2 is a flowchart that illustrates operation of the processor circuitry in the embodiment of FIG. 1.

FIG. 2 illustrates operation of apparatus 10 in an application for monitoring oxygen concentration and indicating when such concentration decreases below a single threshold level. Such an application is suitable, for example, in monitoring an oxygen concentrator in home health care applications as described above to indicate when concentrator output decreases below a desired minimum level such as eighty-five percent. Referring to FIG. 2, operation of apparatus 10 is initialized at 50 by application of electrical power or resetting of processor 22, and the prestored calibration indicia in memory 24 is read by processor 22. If input 34 (FIG. 1) indicates at 52 that apparatus 10 is in a calibration mode of operation, sensor output calibration indicia is read by processor 22 at 54 and stored in memory 24. Processor 22 then proceeds to the monitoring mode of operation 56, in which the output of sensor element 14 is periodically sampled through convertor 20. This operation is illustrated in FIGS. 3A and 3B.

Figure 3A:
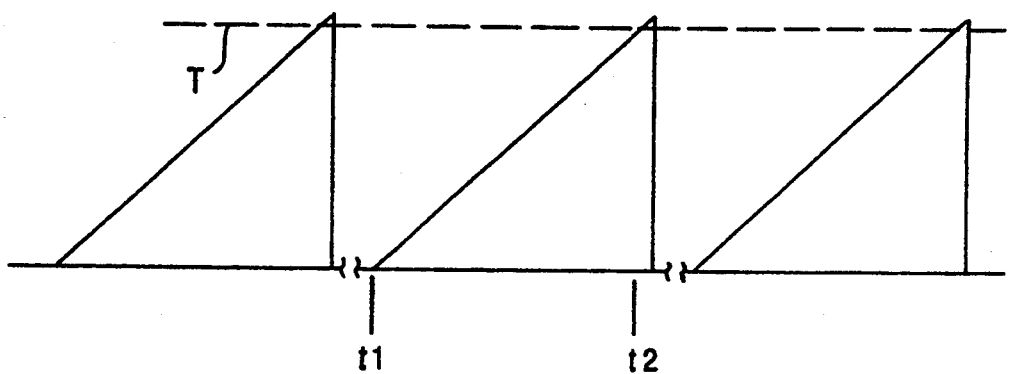
FIGS. 3A and 3B are timing diagrams that illustrate output of the oxygen sensor in the embodiment of FIG. 1.
Figure 3B:
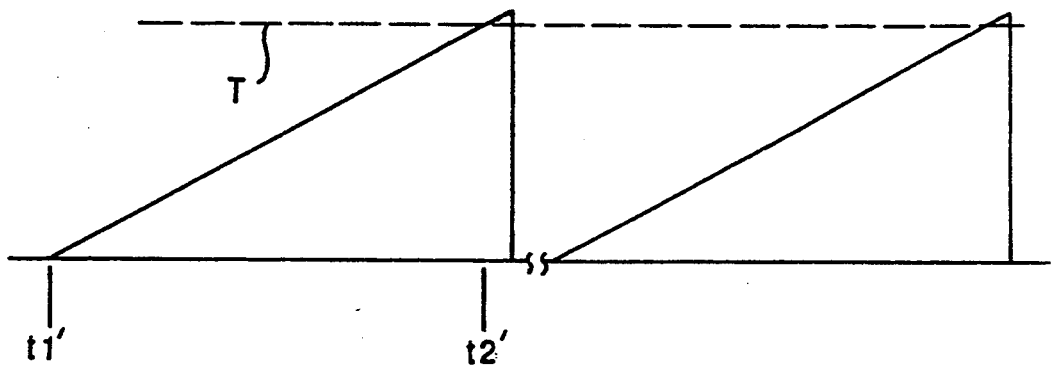

FIG. 3A illustrates the output of convertor 20 when oxygen concentration at sensor 12 is relatively high and above the minimum desired threshold. At time t1, processor 22 initializes operation at convertor 20, and the ramp output of convertor 20 is monitored to a time t2 at which such output exceeds a threshold T. FIG. 3B illustrates a similar conversion process at lower oxygen concentration, in which processor 22 again initiates operation of convertor 20 at time t1', and monitors operation of convertor 20 to time t2' at which the output voltage again crosses threshold T. It will be noted in FIGS. 3A and 3B that total time required for the convertor output to exceed threshold T is relatively short (t2-t1) at high oxygen concentration (FIG. 3A), but it is relatively long (t2'-t1') at lower oxygen concentration (FIG. 3B). This convertor operating time is a continuous monotonic function of oxygen concentration at sensor 12. Processor 22 may thus determine when oxygen concentration decreases below the desired minimum threshold, eighty-five percent in this example, when the time required for such conversion exceeds the conversion time determined and stored during the calibration operation. It will be appreciated, of course, that other methods of sensor output conversion, such as pulsed frequency modulation at constant duty cycle, or pulsed duty cycle modulation at constant frequency, may also be employed.

Returning to FIG. 2, processor 22 monitors operation of convertor 20 as described above, and compares the convertor output at 58 to the calibration indicia prestored in memory 24 to determine whether oxygen concentration is greater than or less than the calibration threshold level. If monitored oxygen concentration is above the desired minimum threshold level, a timer TLEDON is set equal to zero at 60, LED 28 is turned off, alarm 32 is turned off, and operation cycles to the beginning 56 of the monitoring phase. Thus, as long as oxygen concentration remains above the calibrated minimum desired level, operation continues in this loop. However, in the event that oxygen concentration falls below the desired minimum level, operation proceeds to a step 62 at which the oxygen sensor/convertor output is examined to determine if a probable sensor failure is indicated. This is accomplished by comparing the oxygen concentration indicated by the sensor and convertor with the normal expected operating range. For example, in oxygen concentrator applications for home medical care discussed herein by way of example, oxygen concentration would not be expected to exceed a level of ninety-five percent, or decrease below a level of twenty-one percent, which is the concentration of oxygen in air. Hence, if the output of sensor 12 and convertor 20 indicates an oxygen concentration greater than ninety-five percent or less than twenty-one percent, this is interpreted by processor 22 as indicating probable failure at the sensor, such as a failure at heater element 16. In such an event 64, processor 22 flashes LED 28 through driver 26. On the other hand, if a sensor failure is not indicated, then LED 28 is continuously energized at 66. In either event, timer TLEDON is incremented at 68. The TLEDON timer is then examined at 70 to determine whether the LED has been energized, either continuously or flashing for fifteen minutes. If so, buzzer 32 is energized at 72. In either event, operation is cycled to the monitoring step 56.

In accordance with a feature of the invention hereinabove described, the calibration of the desired minimum and/or maximum oxygen concentration threshold(s) is accomplished at the factory at the time of apparatus manufacture, and cannot be readily reprogrammed in the field. This feature helps prevent accidental or intentional reprogramming of the monitor. However, a technician may selectively reprogram the monitor in the field by inserting a DIP switch 48 in socket 40, and by appropriately setting the various elements in switch 48 while exposing sensor 12 to one or more known threshold concentration levels. Upon completion of this operation, DIP switch 48 is removed by the technician so that apparatus 10 is again relatively tamperproof.

It is claimed:

1. Apparatus for monitoring gaseous oxygen concentration comprising:

an oxygen sensor for providing an electrical sensor signal that varies as a function of oxygen concentration at said sensor, processor circuit means responsive to said electrical signal for comparing oxygen concentration indicated by said signal to at least one threshold level, means responsive to said processor circuit means for indicating when oxygen concentration at said sensor departs from said threshold level and means for calibrating said processor circuit means to said at least one threshold level including means for removably connecting said calibrating means to said processor circuit means for controlling calibration of said processor circuit while said sensor is exposed to a gas having an oxygen concentration corresponding to said threshold level.

2. The apparatus set forth in claim 1 wherein said sensor and said processor circuit means are mounted together on a circuit board assembly and wherein said means for removably connecting said calibrating means to said processor circuit comprises a switch socket on said assembly and a switch removably mounted on said socket.

3. The apparatus set forth in claim 1 wherein said calibrating means comprises means for exposing said sensor to gas having an oxygen concentration equal to said threshold level and means responsive to said electrical signal from said sensor for automatically storing calibration indicia indicative of said sensor signal at said threshold concentration level, said processor circuit means including means for retrieving said stored indicia for comparison to said sensor signal to determine when oxygen concentration indicated by said signal departs from said threshold level.

4. The apparatus set forth in claim 3 wherein said sensor and said processor circuit are mounted together on a circuit board assembly having a card-edge contact means along one edge of said assembly which is electrically connected to said processor circuit means.

5. The apparatus set forth in claim 4 wherein said sensor is disposed adjacent to said one edge, and wherein said means for removably connecting said calibrating means to said processor circuit means includes means for mating reception of said card-edge contact means on said calibrating means to control the calibration of said processing circuit means and means for exposing said sensor to a calibration gas having an oxygen concentration equal to said threshold level when the circuit board assembly is inserted in said mating reception means.

* * * * *

UNITED STATES PATENT AND TRADEMARK OFFICE
CERTIFICATE OF CORRECTION

PATENT NO. : 5,402,665

DATED : April 4, 1995

INVENTOR(S) : Russell F. Hart et al

It is certified that error appears in the above-identified patent and that said Letters Patent is hereby
corrected as shown below:

On the title page, Appl. No. "66,275" should read Appl. No. --060,275--.

Signed and Sealed this

Twentieth Day of June, 1995

Attest:

BRUCE LEHMAN

*Attesting Officer*  *Commissioner of Patents and Trademarks*